US00PP21659P2

(12) United States Plant Patent
Sakazaki

(10) Patent No.: US PP21,659 P2
(45) Date of Patent: Jan. 18, 2011

(54) ***CALIBRACHOA* PLANT NAMED 'USCAL48804'**

(50) Latin Name: ***Calibrachoa* sp.**
Varietal Denomination: USCAL48804

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/590,816

(22) Filed: Nov. 14, 2009

(51) Int. Cl.
*A01H 5/00* (2006.01)

(52) U.S. Cl. ..... Plt./413
(58) Field of Classification Search ..... Plt./413
See application file for complete search history.

*Primary Examiner*—Kent L Bell
(74) *Attorney, Agent, or Firm*—C. A. Whealy

(57) ABSTRACT

A new and distinct cultivar of *Calibrachoa* plant named 'USCAL48804', characterized by its compact, mounding and outwardly spreading plant habit; vigorous and freely branching growth habit; dense and bushy appearance; early and freely flowering habit; small light purple-colored flowers with darker purple-colored centers; and good garden and summer performance.

1 Drawing Sheet

Botanical designation: *Calibrachoa* sp.
Cultivar denomination: 'USCAL48804'.

BACKGROUND OF THE INVENTION

The present invention relates to a new and distinct cultivar of *Calibrachoa* plant, botanically known as *Calibrachoa* sp. and hereinafter referred to by the name 'USCAL48804'.

The new *Calibrachoa* plant is a product of a planned breeding program conducted by the Inventor in Higashiomi, Shiga, Japan and Bonsall, Calif. The objective of the breeding program is to create new *Calibrachoa* plants with uniform plant habit, freely branching growth habit, attractive small flowers and good summer performance.

The new *Calibrachoa* plant originated from a cross-pollination made by the Inventor on May 8, 2005 in Higashiomi, Shiga, Japan of a proprietary seedling selection of *Calibrachoa* sp. identified as code number CJ05-48, not patented, as the female, or seed, parent with a proprietary seedling selection of *Calibrachoa* sp. identified as code number C377-04, not patented, as the male, or pollen, parent. The new *Calibrachoa* plant was discovered and selected by the Inventor as a single flowering plant within the progeny of the stated cross-pollination in a controlled environment in Bonsall, Calif. on Jul. 6, 2006.

Asexual reproduction of the new *Calibrachoa* plant by terminal cuttings in a controlled environment in Bonsall, Calif. since Jul. 10, 2006 has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USCAL48804'. These characteristics in combination distinguish 'USCAL48804' as a new and distinct cultivar of *Calibrachoa:*

1. Compact, mounding and outwardly spreading plant habit.
2. Vigorous and freely branching growth habit; dense and bushy appearance.
3. Early and freely flowering habit.
4. Small light purple-colored flowers with darker purple-colored centers.
5. Good garden and summer performance.

The new *Calibrachoa* plant can be compared to plants of the female parent selection. Plants of the new *Calibrachoa* differ from plants of the female parent selection in the following characteristics:

1. Plants of the new *Calibrachoa* are more freely branching than plants of the female parent selection.
2. Plants of the new *Calibrachoa* have smaller flowers than plants of the female parent selection.
3. Plants of the new *Calibrachoa* and the female parent selection differ in flower color as plants of the female parent selection have pink-colored flowers.

The new *Calibrachoa* plant can be compared to plants of the male parent selection. Plants of the new *Calibrachoa* differ from plants of the male parent selection in the following characteristics:

1. Plants of the new *Calibrachoa* are more mounding than and not as creeping as plants of the male parent selection.
2. Plants of the new *Calibrachoa* and the male parent selection differ in flower color as plants of the male parent selection have apricot-colored flowers.

Plants of the new *Calibrachoa* can be compared to plants of the *Calibrachoa* 'USCALI212-1', disclosed in U.S. Plant Pat. No. 18,421. In side-by-side comparisons conducted in Bonsall, Calif., plants of the new *Calibrachoa* differed from plants of 'USCALI212-1' in the following characteristics:

1. Plants of the new *Calibrachoa* were more compact than and not as vigorous as plants of 'USCALI212-1'.
2. Plants of the new *Calibrachoa* flowered earlier than plants of 'USCALI212-1'.

Plants of the new *Calibrachoa* can also be compared to plants of the *Calibrachoa* 'USCALI48', disclosed in U.S. Plant Pat. No. 15,707. In side-by-side comparisons conducted in Bonsall, Calif., plants of the new *Calibrachoa* differed from plants of 'USCALI48' in the following characteristics:

1. Plants of the new *Calibrachoa* had smaller flowers than plants of 'USCALI48'.
2. Plants of the new *Calibrachoa* and 'USCALI48' flowered earlier than plants of 'USCALI48'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL48804' grown in a container.

The photograph at the top of the sheet comprises a close-up of typical flowers and leaves of 'USCAL48804'.

DETAILED BOTANICAL DESCRIPTION

The aforementioned photographs and following observations, measurements and values describe plants grown in 15-cm containers in Bonsall, Calif., under commercial practice during the summer and early autumn in an outdoor nursery with day temperatures ranging from 18° C. to 38° C. and night temperatures ranging from 9° C. to 18° C. Plants were pinched one time and were three months old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL48804'.

Parentage:

*Female, or seed, parent.*—Proprietary seedling selection of *Calibrachoa* sp. identified as code number CJ05-48, not patented.

*Male, or pollen, parent.*—Proprietary seedling selection of *Calibrachoa* sp. identified as code number C377-04, not patented.

Propagation:

*Type.*—By terminal cuttings.

*Time to produce a rooted young plant, summer.*—About 22 days at air temperatures of 29° C. and soil temperatures of 17° C.

*Time to produce a rooted young plant, winter.*—About 25 days at air temperatures of 21° C. and soil temperatures of 17° C.

*Root description.*—Medium in thickness, fibrous; white in color.

*Rooting habit.*—Freely branching; moderately dense.

Plant description:

*Plant and growth habit.*—Compact, mounding and outwardly spreading plant habit; freely branching habit with about eight primary lateral branches each with multiple secondary lateral branches; pinching enhances branching; vigorous, dense and bushy growth habit.

*Plant height.*—About 10.5 cm.

*Plant diameter.*—About 41 cm.

Lateral branch description:

*Length.*—About 20 cm.

*Diameter.*—About 2 mm.

*Internode length.*—About 1 cm.

*Strength.*—Strong.

*Aspect.*—Initially upright to outwardly spreading.

*Texture.*—Pubescent.

*Color.*—Close to 144A.

Foliage description:

*Arrangement.*—Before flowering, alternate, simple; after flowering, opposite, simple.

*Length.*—About 2 cm.

*Width.*—About 8 mm.

*Shape.*—Elliptical.

*Apex.*—Broadly acute.

*Base.*—Attenuate.

*Margin.*—Entire.

*Texture, upper and lower surfaces.*—Pubescent.

*Venation pattern.*—Pinnate; arcuate.

*Color.*—Developing leaves, upper surface: Close to 137B. Developing leaves, lower surface: Close to 137C. Fully expanded leaves, upper surface: Close to 147B; venation, close to 147C. Fully expanded leaves, lower surface: Close to 147B; venation, close to 147B.

*Petiole.*—Length: About 1 mm. Diameter: About 1 mm. Texture, upper and lower surfaces: Pubescent. Color, upper and lower surfaces: Close to 146C.

Flower description:

*Flower arrangement and habit.*—Single salverform flowers arising from leaf axils; freely flowering habit with usually about 18 to 22 open flowers and flower buds per lateral branch; flowers face upright and outwardly.

*Fragrance.*—None detected.

*Natural flowering season.*—Early flowering habit, plants of the new *Calibrachoa* begin flowering about six weeks after planting; plants flower continuously from spring though the autumn in Southern California.

*Flower longevity.*—Individual flowers last about five to seven days on the plant; flowers persistent.

*Flower diameter.*—About 2.5 cm.

*Flower length (height).*—About 2.5 cm.

*Flower throat diameter.*—About 6 mm.

*Flower tube diameter, base.*—About 2 mm.

*Flower tube length.*—About 1.5 cm.

*Flower bud.*—Shape: Elongated oblong. Length: About 2.1 cm. Diameter: About 6 mm. Color: Close to 69D.

*Corolla.*—Arrangement: Five petals fused at the base and opening into a flared trumpet. Petal lobe length (from throat): About 1.4 cm. Petal lobe width: About 1.7 cm. Petal shape: Roughly obdeltoid. Petal apex: Rounded with a shallow central point. Petal margin: Entire. Petal texture, upper and lower surfaces: Smooth, glabrous. Throat texture: Smooth, glabrous. Tube texture: Pubescent. Color: Petal lobe, when opening, upper surface: Close to 69C. Petal lobe, when opening, lower surface: Close to 69D. Petal lobe, fully opened, upper surface: Close to 75C; color becoming closer to NN155C with development; towards the throat, close to 77A to 77B; venation, close to N77B. Petal lobe, fully opened, lower surface: Close to 75C to 75D; venation, close to N79C.

Throat: Close to 3B; venation, close to N77C. Tube: Close to 2D; venation, close to N77B.

*Calyx.*—Arrangement: One star-shaped calyx tube with five sepals in a single whorl and fused at the base. Sepal length: About 1 cm. Sepal width: About 2 mm. Sepal shape: Lanceolate. Sepal apex: Acute. Sepal margin: Entire. Sepal texture, upper and lower surfaces: Pubescent. Color, upper and lower surfaces: Close to 137A.

*Peduncles.*—Length: About 1.8 cm. Diameter: About 1 mm. Angle: About 45° to 60° from stem axis. Strength: Moderately strong. Texture: Pubescent. Color: Close to 144C.

*Reproductive organs.*—Stamens: Quantity/arrangement: About five per flower. Filament length: About 4 mm. Filament color: Close to 145B. Anther shape: Oval. Anther length: About 1 mm. Anther color: Close to 1D. Pollen amount: Scarce. Pollen color: Close to 1B. Pistils: Quantity: One per flower. Pistil length: About 8 mm. Style length: About 6 mm. Style color: Close to 144D. Stigma shape: Oval. Stigma color: Close to 144A. Ovary color: Close to N144D. Seed/fruit: Seed and fruit development have not been observed on plants of the new *Calibrachoa.*

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have not been observed to be resistant to pathogens and pests common to *Calibrachoa.*

It is claimed:

1. A new and distinct *Calibrachoa* plant named 'USCAL48804' as illustrated and described.

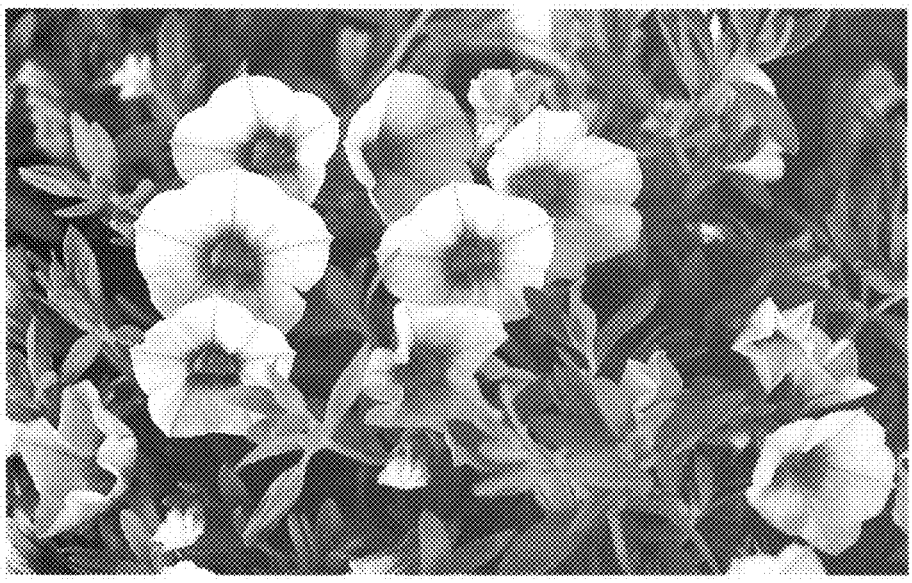
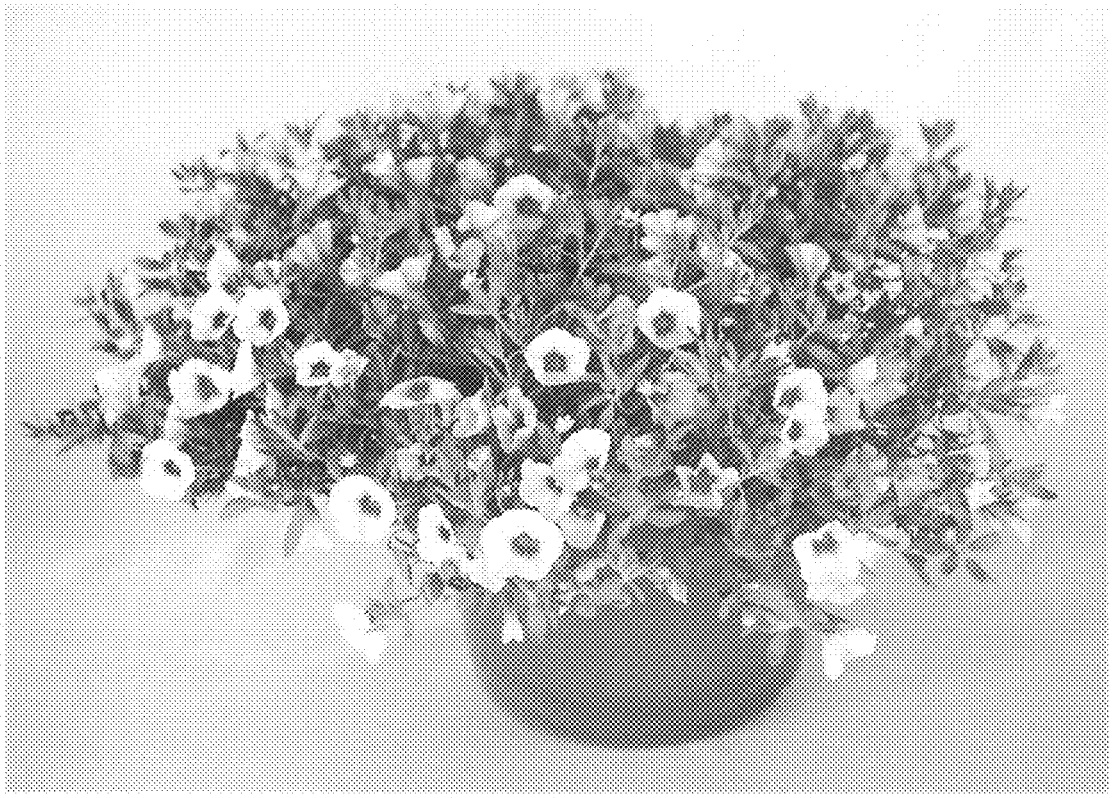

* * * * *